US00PP15104P2

(12) United States Plant Patent
Eggleton

(10) Patent No.: US PP15,104 P2
(45) Date of Patent: Aug. 24, 2004

(54) CONVOLVULUS PLANT NAMED 'MOROCCAN BEAUTY'

(50) Latin Name: *Convolvulus sabatius*
Varietal Denomination: Moroccan Beauty

(76) Inventor: Steven Eggleton, 3 Harris Road, Wonga Park, Melbourne, VIC 3115 (AU)

( * ) Notice: Subject to any disclaimer, the term of this patent is extended or adjusted under 35 U.S.C. 154(b) by 0 days.

(21) Appl. No.: 10/700,796

(22) Filed: Nov. 3, 2003

(51) Int. Cl.[7] ..... A01H 5/00
(52) U.S. Cl. ..... Plt./226
(58) Field of Search ..... Plt./226

(56) References Cited

PUBLICATIONS

UPOV ROM GTITM Computer Database, GTI JOUVE Retrieval Software 2003/05 Citation for 'Moroccan Beauty'.*
Variety: 'Moroccan Beauty' Application No. 2002/131 Plant Varieties Journal vol. 16 (1) p. 20 2003.*

* cited by examiner

*Primary Examiner*—Bruce R. Campell
*Assistant Examiner*—W C Haas

(57) ABSTRACT

A new cultivar of Convolvulus named 'Moroccan Beauty' that is characterized, by prostrate habit, short internodes, medium-green leaves, and violet flowers in spring, summer and fall. In combination these traits set 'Moroccan Beauty' apart from all other existing varieties of Convolvulus known to the inventor.

1 Drawing Sheet

Genus: Convolvulus.
Species: *sabatius.*
Denomination: Moroccan Beauty.

BACKGROUND OF THE INVENTION

The present invention relates to a new and distinct cultivar of Morning Glory that is grown for use as an ornamental landscape plant. The new cultivar is known botanically as *Convolvulus sabatius* and will be referred to hereinafter by the cultivar name 'Moroccan Beauty'.

During the year 2000 growing season, the Inventor produced in a cultivated area of Victoria, Australia, a commercial crop of *Convolvulus sabatius* 'Full Moon' (unpatented) from seed sown in the fall of 2000 (around March 2000) for sale in flower in the late spring and early summer of 2000 (around September 2000). The seed used for this crop had been obtained from the open pollination of plants which had been grown from seed retained from prior crops. In July 2000, which is during the growth period of the 2000 crop, the Inventor observed a seedling, 'Moroccan Beauty', which appeared to be distinguishable from all other seedlings in the crop by exhibiting a uniquely dense and prostrate habit, and short internodes. The Inventor presumes that 'Moroccan Beauty' is a mutant seedling that resulted from the open pollination between random parents, male and female, of *Convolvulus sabatius* 'Full Moon' (seed strain). The Inventor removed 'Moroccan Beauty' from the remaining crop in July 2000 and immediately asexually propagated 'Moroccan beauty' using vegetative stem cuttings. Since that time, under careful observation, the distinguishing characteristics have been determined stable, uniform and true to type in successive generations.

'Moroccan Beauty' exhibits medium-green foliage, and violet flowers. The parent plants, presumed both to be Convolvulus 'Full Moon', exhibit semi-prostrate habit and long internodes. 'Moroccan Beauty' is unique and distinguishable from the parent plants by short internodes and distinctly prostrate habit. The closest comparison plants are Convolvulus 'Full Moon' and Convolvulus 'White Gladys' (unpatented). 'Moroccan Beauty' is unique and distinguishable from 'White Gladys' by flower color. The flowers of 'White Gladys' are white in color, whereas the flowers of 'Moroccan Beauty' are violet in color.

SUMMARY OF THE INVENTION

The following represent the distinguishing characteristics of the new Convolvulus cultivar 'Moroccan Beauty'. In combination these traits set 'Moroccan Beauty' apart from all other existing varieties of Convolvulus known to the inventor. 'Moroccan Beauty' has not been tested under all possible conditions and phenotypic differences may be observed with variations in environmental, climatic, and cultural conditions, however, without any variance in genotype.

1. Convolvulus 'Moroccan Beauty' exhibits violet flowers in spring, summer and fall.
2. Convolvulus 'Moroccan Beauty' exhibits a prostrate growth habit.
3. Convolvulus 'Moroccan Beauty' exhibits a growth habit with short internodes.
4. Convolvulus 'Moroccan Beauty' exhibits medium-green foliage.
5. Convolvulus 'Moroccan Beauty' is evergreen.
6. Convolvulus 'Moroccan Beauty' is 80–100 cm. in diameter and 6 cm. in height at maturity.
7. Convolvulus 'Moroccan Beauty' is hardy to USDA Zone 8.
8. Convolvulus 'Moroccan Beauty' is an ornamental landscape plant suitable for use as a groundcover and as a hanging basket.

BRIEF DESCRIPTION OF THE DRAWING

The accompanying color drawing illustrates the overall appearance of the new Convolvulus variety 'Moroccan Beauty' showing the colors as true as it is reasonably possible to obtain in colored reproductions of this type. Colors in the drawing may differ from the color values cited in the detailed botanical description, which accurately describe the actual colors of the new variety 'Moroccan Beauty'. The plant in the drawing is 6-months-old and was grown out-of-doors in a 1-liter container. The drawing on sheet 1 illustrates the entire plant in bloom from a side perspective. The drawing was made using conventional techniques and although colors may appear different from actual colors due to light reflectance, they are as accurate as possible by conventional photography.

BOTANICAL DESCRIPTION OF THE PLANT

The following is a detailed description of the Convolvulus cultivar named 'Moroccan Beauty'. Data was collected in Arroyo Grande, Calif. from mature plants grown out-of-doors and planted in the ground from 1-liter containers. Color determinations are in accordance with The Royal Horticultural Society Colour Chart except where general color terms of ordinary dictionary significance are used. The growing requirements are similar to the species and there are no disease problems known to the inventors.

Botanical classification: Convolvulus 'Moroccan Beauty'.
Species: *sabatius.*
Common name: Morning glory.
Commercial classification: Ornamental.
Type: Perennial.
Use: Suitable for use as a groundcover or as a hanging basket.
Parentage: 'Moroccan Beauty' is a mutant seedling that resulted from open pollination between the following parent plants:
*Female parent.*—*Convolvulus sabatius* 'Full Moon'.
*Male parent.*—*Convolvulus sabatius* 'Full Moon'.
Vigor: Moderate.
Growth habit: Prostrate.
Plant shape: Circular.
Plant form: Flat.
Height: 6 cm. in height.
Width: 80–100 cm. in diameter.
Hardiness: USDA Zone 8.
Propagation: Vegetative stem cuttings.
Root system: Fine.
Cultural requirements: Plant in full sun or light shade, and well-drained soil with moderate water.
Seasonal interest: Violet flowers in spring, summer and fall.
Time and temperature to develop roots on initial cutting: 14–21 days are needed to develop roots on initial cuttings at air temperature of 15° to 25° Centigrade.
Time to develop to commercial container size: 6–9 months are needed to produce a 1-liter container plant from a rooted cutting.
Special growing requirements or growing problems: None known to the inventor.
Disease and pest susceptibility: Tolerant of diseases and pests common to other Convolvulus.
Stem:
*Branching habit.*—Trailing branches.
*Stem diameter.*—0.30 cm. in diameter.
*Stem length.*—23 cm. in length.
*Internode length.*—1 cm. between nodes.
*Stem shape.*—Oval.
*Stem surface.*—Pubescent.
*Stem color.*—138C.

Foliage:
*Type.*—Evergreen.
*Leaf arrangement.*—Alternate.
*Leaf division.*—Simple.
*Leaf margin.*—Entire.
*Leaf surface* (*adaxial and abaxial*).—Pubescent.
*Leaf shape.*—Obicular.
*Leaf apex.*—Truncate.
*Leaf base.*—Cordate.
*Leaf attachment.*—Petiolate.
*Stipules.*—Absent.
*Petiole dimensions.*—2 mm. in length and 1 mm. in width.
*Petiole color.*—144A.
*Leaf length.*—Individual leaf length on an individual plant ranges from 1.50 cm. to 2.50 cm. in length.
*Leaf width.*—Individual leaf width on an individual plant ranges from 1.50 cm. to 2.50 cm. in width.
*Leaf color* (*adaxial surfaces*).—Individual leaf color on adaxial surfaces ranges from 138A to 139A on an individual plant.
*Leaf color* (*abaxial surfaces*).—Individual leaf color on abaxial surfaces range from 138B to 139B on an individual plant.

Flower:
*Inflorescence.*—Solitary flower.
*Shape of flower.*—Funnelform.
*Dimensions of flower.*—3 cm. in diameter, 2.25 cm. in length, and 2.25 cm. in depth.
*Aspect.*—Facing outward and upward.
*Color of flower* (*adaxial surface*).—85A.
*Color of flower* (*abaxial surface*).—85D.
*Flower surfaces* (*abaxial and adaxial*).—Glabrous.
*Flower margin.*—Entire.
*Bud dimensions.*—10 mm. in length and 3 mm. in width.
*Bud shape.*—Elongated oval.
*Bud color.*—150D.
*Bud apex.*—Acute.
*Peduncle dimensions.*—7 mm. in length and 1 mm. in width.
*Peduncle surface.*—Pubescent.
*Peduncle color.*—144A.
*Bracteoles.*—Present.
*Number of bracteoles.*—Two per petiole.
*Bracteole dimensions.*—7 mm. in length and 2 mm. in width.
*Bracteole shape.*—Lanceolate.
*Bracteole attachment.*—Sessile.
*Bracteole apex.*—Acute.
*Bracteole margin.*—Entire.
*Bracteole surface.*—Pubescent.
*Bracteole color.*—144A.
*Calyx dimensions.*—6 mm. in length and 5 mm. in width.
*Sepals fused or unfused.*—Basally fused.
*Number of sepals.*—Five sepals.
*Sepal color* (*adaxial and abaxial surfaces*).—Sepal base is 148C and sepal tip is 148A.
*Sepal surfaces* (*adaxial and abaxial surfaces*).—Pubescent.
*Sepal margin.*—Entire.
*Blooming period.*—May to November.

Reproduction organs:
*Stamens.*—Five in number.

*Stamen shape.*—Filaments that are adnate to corolla at base of stamen.
*Stamen color.*—155A.
*Stamen dimensions.*—7 mm. in length and 0.50 mm. in width.
*Anther shape.*—Sagitate.
*Anther color.*—155A.
*Anther dimensions.*—1.25 mm. in length and 1 mm. in width.
*Pollen amount.*—Large amount.
*Pollen color.*—155A.
*Pistil shape.*—Filament.
*Pistil length.*—10 mm. in length.
*Pistil color.*—155A.
*Ovary.*—Present.
*Ovary color.*—151C.
*Ovary position.*—Superior.
*Ovary shape.*—Globular.
*Ovary dimensions.*—3 mm. in width and 3 mm. in height.

Seed: No seed production has been observed to date.

It is claimed:

1. A new and distinct variety of Convolvulus plant named 'Moroccan Beauty' as described and illustrated herein.

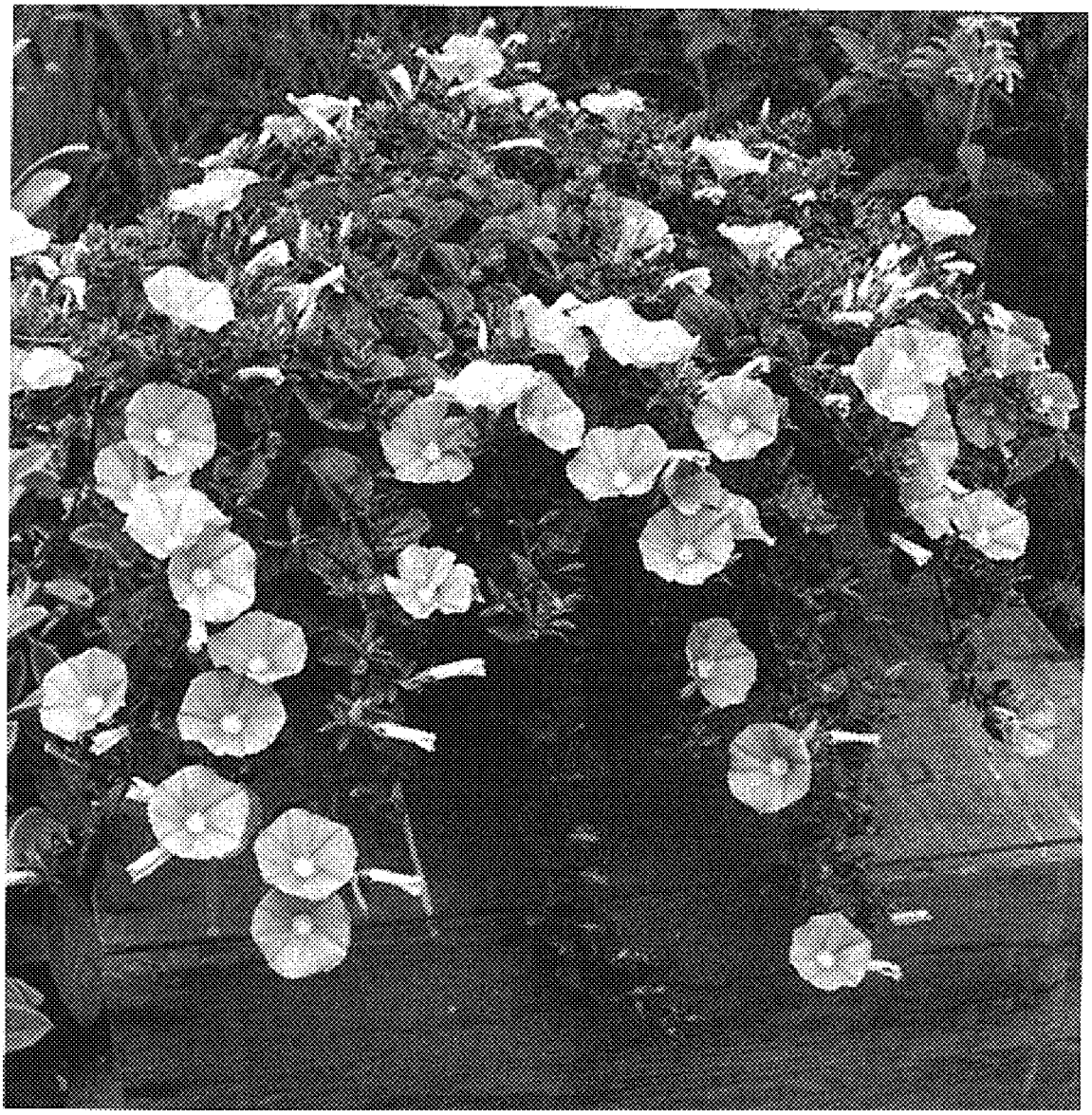

* * * * *